United States Patent
Corma Canós et al.

(10) Patent No.: US 10,005,076 B2
(45) Date of Patent: Jun. 26, 2018

(54) SYNTHESIS OF SAPO-18 AND THE CATALYTIC APPLICATIONS THEREOF

(71) Applicants: CONSEJO SUPERIOR DE INVESTIGACIONES CIENTÍFICAS, Madrid (ES); UNIVERSITAT POLITÈCNICA DE VALÈNCIA, Valencia (ES)

(72) Inventors: Avelino Corma Canós, Valencia (ES); Manuel Moliner Marín, Valencia (ES); Raquel Martínez Franco, Valencia (ES)

(73) Assignees: Consejo Superior de Investigaciones Científicas, Madrid (ES); Universitat Politècnica de València, Valencia (ES)

( * ) Notice: Subject to any disclaimer, the term of this patent is extended or adjusted under 35 U.S.C. 154(b) by 0 days. days.

(21) Appl. No.: 15/315,200

(22) PCT Filed: Jun. 3, 2015

(86) PCT No.: PCT/ES2015/070438
§ 371 (c)(1),
(2) Date: May 30, 2017

(87) PCT Pub. No.: WO2015/185781
PCT Pub. Date: Dec. 10, 2015

(65) Prior Publication Data
US 2017/0259253 A1 Sep. 14, 2017

(30) Foreign Application Priority Data

Jun. 3, 2014 (ES) .................................. 201430852

(51) Int. Cl.
| | | |
|---|---|---|
| C01B 39/54 | (2006.01) |
| B01J 29/85 | (2006.01) |
| B01J 37/04 | (2006.01) |
| B01J 37/10 | (2006.01) |
| B01J 37/00 | (2006.01) |
| C07D 211/14 | (2006.01) |
| C30B 7/10 | (2006.01) |
| C30B 29/14 | (2006.01) |
| B01J 29/74 | (2006.01) |
| B01J 29/72 | (2006.01) |
| B01J 29/76 | (2006.01) |
| B01J 29/70 | (2006.01) |

(52) U.S. Cl.
CPC ............ *B01J 29/85* (2013.01); *B01J 37/009* (2013.01); *B01J 37/0018* (2013.01); *B01J 37/04* (2013.01); *B01J 37/10* (2013.01); *C01B 39/54* (2013.01); *C07D 211/14* (2013.01); *C30B 7/10* (2013.01); *C30B 29/14* (2013.01); *B01J 29/7015* (2013.01); *B01J 29/723* (2013.01); *B01J 29/743* (2013.01); *B01J 29/763* (2013.01)

(58) Field of Classification Search
CPC .................................. C01B 39/54; B01J 29/85
See application file for complete search history.

(56) References Cited

U.S. PATENT DOCUMENTS

| 5,324,493 A | 6/1994 | Mueller et al. | |
| 6,537,941 B2* | 3/2003 | Janssen | B01J 29/85 502/20 |
| 6,685,905 B2* | 2/2004 | Mertens | B01J 29/85 423/306 |
| 7,622,417 B2* | 11/2009 | Mertens | B01J 29/83 423/111 |
| 2009/0238745 A1 | 9/2009 | Mertens | |

FOREIGN PATENT DOCUMENTS

| WO | 2007130231 | 10/2013 |
| WO | 2013159828 | 10/2013 |

OTHER PUBLICATIONS

Mathiesen, K. et al., "The influence of silicon on the catalytic properties of CuSAPO-5 towards the selective reduction of NOx in the presence of propene," Project report for SNBL BM01b, Feb. 2005, 5 pp.

International Search Report for PCT/ES2015/070438 dated Jul. 13, 2015, 4 pp.

Martinez-Franco, R. et al., "Direct synthesis design of Cu-SAPO-18, a very efficient catalyst for the SCR of NOx," J. Catalysis, 2014, 319:36-43.

European Search Report for European Application 15802461.2 dated Dec. 6, 2017.

Ye, Q. et al. "Activity, propene poisoning resistance, and hydrothermal stability of copper exchange chabazite-like zeolite catalysts for SCR of NO with ammonia in comparison to Cu/ZSM-5,"Applied Catalysis A: General, 2012 (47);24-34.

Chen, J. et al., "SAPO—18 catalysts and their Bronsted acid sites," J. Phys. Chem., 1994(98):10216-10224.

* cited by examiner

*Primary Examiner* — David M Brunsman
(74) *Attorney, Agent, or Firm* — Suzannah K. Sundby, Esq.; Canady + Lortz LLP

(57) ABSTRACT

Synthesis of the silicoaluminophosphate and metal silicoaluminophosphate polymorphs of the molecular sieve SAPO-18 using cyclic quaternary ammoniums as organic structure-directing agents (OSDA) and use thereof as a catalyst.

24 Claims, 2 Drawing Sheets

SYNTHESIS OF SAPO-18 AND THE CATALYTIC APPLICATIONS THEREOF

FIELD OF THE ART

The present invention relates to a new procedure for the synthesis of the SAPO-18 molecular sieve in its silicoaluminophosphate and metal silicoaluminophosphate form (Me-SAPO-18) using cyclic quaternary ammonium compounds as structure-directing agents. This procedure involves combining the various sources required for preparing a silicoaluminophosphate (SAPO), such as silicon, aluminium and phosphorus, with a cyclic quaternary ammonium and, in the case of preparation of Me-SAPO-18, a source of a metal. The present invention, in addition to relating to the synthesis method, also relates to the application of said materials as catalysts.

BACKGROUND OF THE INVENTION

In 1982, UOP first described the preparation of a family of molecular sieves, called aluminophosphates (AlPOs) (Wilson, S T, et al. J. Am Chem. Soc. 1982, 104, 1146). The composition of the microporous crystal structure of these materials consists of Al and P tetrahedra that share vertices via O atoms. Silicoaluminophosphates (SAPOs) are a particular case of AlPOs, where some of the atoms of the structure are partially substituted by silicon atoms (Chen, J S et al. J. Phys. Chem., 1994, 98, 10216). This substitution can occur via two different mechanisms: a) replacement of a P atom by a Si atom, generating a negative charge in the structure (isolated silicon), or b) replacement of one atom of Al and one atom P by two Si atoms, giving rise to the formation of silicon-rich domains (silicon islands). Only when the silicon is in isolation, SAPOs exhibit excellent cation exchange capacity, allowing the presence of different active species suitable for various catalytic applications. Possibly the most common SAPOs are in protonated form. The protons associated with the replacement of the Si structure gives these materials high acidity, which can be applied as acid catalysts in catalytic processes, such as synthesis of methanol to olefins (S W Kaiser, U.S. Pat. No. 4,499,327; 1985).

Thus, the distribution of silicon in the walls of the SAPOs is arguably the most important factor for controlling the acidity of these materials. The organic structure-directing agent (OSDA) used in the preparation of SAPOs not only influences the crystallization of a given structure, but also the positioning and coordination of the silicon atoms in the crystal structure of the molecular sieve.

Silicoaluminophosphate SAPO-18 is a three-dimensional small-pore molecular sieve (eight-atom channel openings with pore diameters of approximately 3.8 Å) with large cavities in its interior. As observed in the literature, the conventional preparation of SAPO-18 was carried out using the organic molecule N,N-diisopropylethylamine as OSDA (Chen et al Catal Lett, 1994, 28, 241; Chen et al. J. Phys Chem, 1994, 98, 10216; Hunger et al, Catal Lett, 2001, 74, 61; Wragg et al J. Catal, 201 1, 397). This SAPO-18 synthesis procedure makes it possible to obtain silicoaluminophosphate with mixtures of isolated silicon and silicon islands. The presence of silicon islands confers lower Brönsted acidity to said SAPO-18s (Chen et al J. Phys Chem, 1994, 98, 10216; Hunger et al, Catal Lett, 2001, 74, 61; Wragg et al. J. Catal., 201 1, 397). Recently, the synthesis of SAPO-18 using tetraethylammonium as OSDA has been disclosed, but this synthesis method also shows large silicon environments forming islands (Fan et al., J. Mater. Chem., 2012, 22, 6568), and therefore, lower Brönsted acidity.

Other cations, different to the protons, may also be introduced in the SAPOs. Conventionally, the introduction of the metal cation species in SAPOs (Me-SAPO) is carried out via post-synthetic cation exchange procedures. However, said post-synthetic procedures require numerous intermediate stages to obtain the Me-SAPO: hydrothermal synthesis of SAPO, calcination, transformation into the ammonium form (if required), cation exchange of the metal and, finally, calcination to obtain the final Me-SAPO. All of these intermediate steps result in an increase in the cost of the synthesis of the corresponding Me-SAPO.

Furthermore, when introducing a cationic metal in extra-network positions in a SAPO, it is very important that the silicon species be isolated in the crystal lattice, because they will generate the negative charges that will make it possible to compensate and stabilise the positive charges of the cationic metals.

In recent years, the preparation of metal-substituted molecular sieves, and particularly, molecular sieves with a small pore size and large cavities in the substituted cationic copper structure have received much attention because of their high activity and stability for the selective catalytic reduction (SCR) of nitrogen oxides (NOx) with ammonia or hydrocarbons in the presence of oxygen (I. Bull, et al., U.S. Pat. No. 0,226,545, 2008). In this regard, the formation of NOx during combustion of fossil fuels, especially in transport is one of the great current environmental challenges.

Recently, the introduction of Cu cationic species in the SAPO-18 materials by post-synthetic cation exchange has been described (Li et al WO2008/1 18434; Ye et al. Appl Catal A 2012, 427, 34; Ye et al., CN 102 626 653). However, the synthesis of the molecular sieve Cu-SAPO-18 requires a considerable number of steps to finally obtain the catalyst: hydrothermal synthesis of SAPO-18, removal by thermal treatment of organic matter confined in the interior of the pores/cavities during synthesis, prior cation exchange with ammonium cations, cation exchange with copper and, finally, calcination to obtain the Cu-SAPO-18. This material shows good catalytic activity for NOx SCR, but less hydrothermal stability than other catalysts, such as Cu-SSZ-13 or Cu-SAPO-34 (Ye et al. Appl. Catal. A, 2012, 427, 34). The fact that the synthesis of the original SAPO-18 is carried out using the procedure described in the reference (Chen et al. J. Phys. Chem. 1994, 98, 10216), where part of the silicon is forming silicon islands, prevents good stabilisation of extra-framework cations and, therefore, the corresponding Cu-SAPO-18 is less stable.

DESCRIPTION OF THE INVENTION

The present invention relates to a procedure for the synthesis of SAPO-18, which may comprise, at least, the following steps:
i) Preparation of a mixture containing at least water, at least one source of silicon, at least one source of aluminium, at least one source of phosphorus, one or more OSDAs wherein at least one of them is a cyclic quaternary ammonium and where the final synthesis mixture has the following molar composition:

where a is comprised between the interval 0.01 to 0.3, preferably between 0.03 to 0.3 and, more preferably, between 0.05 to 0.3;

where b is comprised between the interval 0.2 to 0.49, preferably between 0.2 to 0.47 and, more preferably, between 0.2 to 0.45;

where c is comprised between the interval 0.001 to 2, preferably between 0.1 to 1 and, more preferably, between 0.2 to 0.7;

where d is comprised between the interval of 1 to 200, preferably between 2 to 100 and, more preferably, between 3 to 50.

ii) Crystallization stage in which the mixture is hydrothermally treated at a temperature comprised between 80-200° C. until the crystallization of the material.

iii) Recovery of the crystalline material.

The main objectives of the present invention will perform an efficient synthesis process that allows, on one hand, the synthesis of the silicoaluminophosphate SAPO-18 form with a good distribution of silicon in isolated positions to enhance their Brönsted acidity and, on the other, the synthesis in a single step (direct synthesis) of the metalosilicoaluminophosphate form of SAPO-18 (Me-SAPO-18) with metal cationic species in extra-framework positions and isolated silicon in the crystal lattice. Thus, we will not only reduce the high number of stages required for the synthesis of Me-SAPO-18, but also improve the hydrothermal stability of the cationic metal species and, therefore, the hydrothermal stability of the material.

This synthesis procedure is carried out using different sources required in the preparation of a conventional SAPO, such as any source of silicon, aluminium and phosphorus, together with at least one OSDA, at least one of which is a cyclic quaternary ammonium, preferably selected from N,N-dimethyl-3,5-dimethyl (DMDMP), N,N-diethyl-2,6-dimethylpiperidine (DEDMP), N,N-dimethyl-2,6-dimethylpiperidine, N-ethyl-N-methyl-2,6-dimethylpiperidine and combinations thereof, and any variation thereof. The other OSDA, if any, may be any other cyclic quaternary ammonium or any other organic molecule, such as for example, any amine, quaternary ammonium, phosphine, phosphonium, phosphazene and combinations thereof.

According to a particular embodiment, the crystallization step described in (ii) may be carried out in autoclaves under both static and dynamic conditions. Furthermore, the temperature of the crystallization process may be comprised, preferably, in the temperature range between 100 and 200° C., more preferably between 130 and 190° C. and, more preferably, between 150 and 190° C.; and the crystallization time may be between 1 hour and 50 days, preferably between 1 and 10 days, and more preferably between 2 to 8 days. It is important to note that the components of the synthesis mixture may come from different sources and, depending on this, crystallization time and conditions may vary.

According to the procedure of the present invention, SAPO-18 crystals may be added to the final synthesis mixture of (i) as seed and may reach up to 25% by weight of the total oxides introduced in the synthesis.

After the crystallization process, the crystals of the SAPO-18 material are separated from the mother liquor and recovered. The solid may be washed and separated from the mother liquor using different techniques, preferably the decantation, filtration, ultrafiltration, centrifugation or other solid-liquid separation techniques and combinations thereof.

According to a particular embodiment, the objective may be to produce the calcinated crystalline material. In this case, the procedure described according to the present invention further comprises a step of removing the organic matter occluded inside the material, which can be performed using a technique selected from among extraction, thermal treatment and combinations thereof at temperatures above 25° C., during periods comprised between 2 minutes and 25 hours.

The material produced through this invention can be pelletized in accordance with known techniques.

According to a preferred embodiment, the synthesis procedure described above can further comprise at least one source of metal where the final synthesis gel would have the following molar composition:

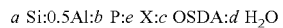

$a$ Si:0.5Al:$b$ P:$e$ X:$c$ OSDA:$d$ H$_2$O where a is comprised between the interval 0.01 to 0.3, preferably between 0.03 to 0.3 and, more preferably, between 0.05 to 0.3;

where b is comprised between the interval 0.2 to 0.49, preferably between 0.2 to 0.47 and, more preferably, between 0.2 to 0.45;

where c is comprised between the interval 0.001 to 2, preferably between 0.1 to 1 and, more preferably, between 0.2 to 0.7;

where d is comprised between the interval of 1 to 200, preferably between 2 to 100 and, more preferably, between 3 to 50;

where e is comprised between the interval of 0.00 to 0.6, preferably between 0.01 and 0.4 and, more preferably, between 0.015 to 0.2.

This embodiment describes a direct synthesis procedure in which the Me-SAPO-18 product is obtained, where Me is a metal. Preferably, said metal is selected between Cu, Ni, Fe, Pt, Pd, Mn, Ca, Mg, Zn, Cd, Co, Ti, Sn and combinations thereof. Preferably, said metal is Cu.

Additionally, the present invention also relates to the product obtained according to the procedure described above, which may have the following molar composition:

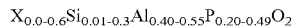

$X_{0.0-0.6}Si_{0.01-0.3}Al_{0.40-0.55}P_{0.20-0.49}O_2$

According to a particular embodiment, the product obtained according to the procedure of the present invention may have the following molar composition:

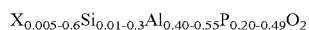

$X_{0.005-0.6}Si_{0.01-0.3}Al_{0.40-0.55}P_{0.20-0.49}O_2$

According to the present invention, X is a metal selected from Cu, Ni, Fe, Pt, Pd, Mn, Ca, Mg, Zn, Cd, Co, Ti, Sn and combinations thereof and, according to a particular embodiment, X is Cu.

The source of metal may be any precursor thereof, such as for example nitrates, oxalates, sulphates, organometallic complexes and combinations thereof, among others.

In particular, the Me-SAPO-18 direct synthesis procedure described above uses Cu as a metal for the direct synthesis of Me-SAPO-18. According to said procedure, any source of copper may be used to prepare Cu-SAPO-18, including the use of Cu organometallic complexes. In this regard, any amine or mixtures of amines capable of forming organometallic complexes with copper, can be used regardless of the number of N atoms in their structure, regardless of their form (cyclic, linear, branched, . . . ) and regardless of the nature of the amine (primary, secondary, tertiary). Examples of amines may be tetraethylenepentamine (TEPA), triethylenetetramine (TETA), 1,4,8,11-tetraazacyclotetradecane or 1,4,8,11-tetramethyl-1,4,8,11-tetraazacyclotetradecane and combinations thereof, inter alia.

According to a particular embodiment, the product obtained has the metal in extra-frameworkpositions directly and in a single stage, avoiding the use of successive post-synthetic steps. The combination of OSDAs described, at least one cyclic quaternary ammonium, allows excellent distribution of the silicon centres in an isolated manner in the SAPO-18 structure, making it possible to compensate and stabilise the positive charges of the cationic extra-framework metals.

The present invention also relates to the use of the materials described above and obtained according to the process of the present invention as catalysts for converting feeds formed from organic compounds into higher value-added products, or for the disposal/separation of the reactive current by contacting said feed with the described material in its active form.

According to a particular embodiment, Me-SAPO-18 can be used as catalysts in selective catalytic reduction (SCR) reactions of NOx (nitrogen oxides) in a gas stream. It has been found that Cu-SAPO-18 gives very good results in this type of reactions. In particular, the Cu-SAPO-18 molecular sieves according to the present invention are used as catalysts for SCR of NOx in the presence of a reducing agent such as ammonia, urea and/or hydrocarbons.

According to a preferred embodiment, according to the procedure of the present invention, the synthesis of Cu-SAPO-18 is achieved in a single stage by preferably positioning the Cu cation in extra-framework positions, which gives the material specific qualities, both activity and hydrothermal stability, for the selective catalytic reduction reaction of nitrogen oxides.

Throughout the description and claims, the word "comprise" and its variants are not intended to exclude other technical characteristics, additives, components or steps. For persons skilled in the art, other objects, advantages and characteristics of the invention will arise partly from the description and partly from the practice of the invention.

EXAMPLES

Figure 1:
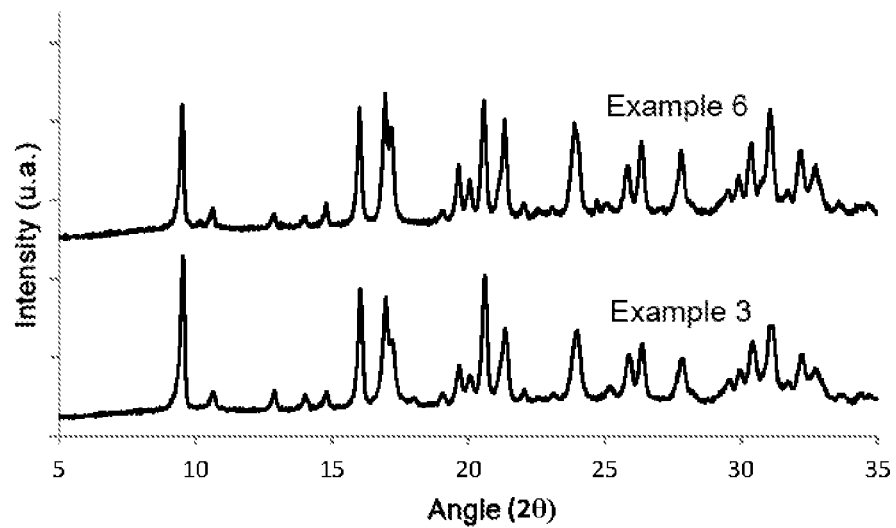
FIG. 1: X-ray diffraction patterns of the solid synthesized in examples 3 and 6 described herein.

The following examples are provided by way of illustration and are not intended to be limiting of the present invention.

Example 1

Synthesis of OSDA iodide
N,N-dimethyl-3,5-dimethylpiperidine (DMDMP)

10 g of 3,5-dimethylpiperidine (Sigma-Aldrich, ≥96% by weight) are mixed with 19.51 g of potassium bicarbonate (KHCO$_3$ Sigma-Aldrich; 99.7% by weight) and dissolved in 140 ml of methanol. Next, 54 ml of methyl iodide (CH$_3$I, Sigma-Aldrich, ≥99% by weight) are added and the resulting mixture is kept under stirring for 5 days at room temperature. After this time, the reactive mixture was filtered to remove the potassium bicarbonate. The filtered solution is partially concentrated by rotary evaporation. Once the methanol has been partially evaporated, the solution is washed several times with chloroform and magnesium sulphate (MgSO$_4$ Sigma-Aldrich, ≥99.5% by weight) is added. The mixture is filtered to remove the magnesium sulphate. Ammonium salt is obtained by precipitation with diethyl ether and subsequent filtration. The final yield of iodide N,N-dimethyl-3,5-dimethylpiperidine is 85%.

To prepare the hydroxide form of the above organic salt: 10.13 g of the organic salt are dissolved in 75.3 g of water. Next, they are added with 37.6 g of an anion exchange resin (Dower SBR) and the resulting mixture is kept under stirring for 24 hours. Finally, the solution is filtered and N,N-dimethyl-3,5-dimethylpiperidine hydroxide is obtained (with an exchange percentage of 94%).

Example 2

Synthesis of OSDA iodide
N,N-diethyl-2,6-dimethylpiperidine (DEDMP)

36 g of cis-2,6-dimethylpiperidine (Sigma-Aldrich, 98% by weight) are mixed with 320 ml of methanol and 64 g of potassium bicarbonate (KHCO$_3$ Sigma-Aldrich; 99.7% by weight). Subsequently, 200 g of ethyl iodide (Sigma-Aldrich, 99% by weight) are added and the resulting mixture is refluxed for 5 days. After this time, the reaction mixture is filtered to remove potassium bicarbonate. The filtered solution is partially concentrated by rotary evaporation. Once the methanol is partially evaporated, the solution is washed several times with chloroform and added with magnesium sulphate (MgSO$_4$ Sigma-Aldrich, ≥99.5% by weight). The mixture is filtered to remove the magnesium sulphate. Ammonium salt is obtained by precipitation with diethyl ether and subsequent filtration. The final yield of N,N-diethyl-2,6-dimethylpiperidine iodide is 75%.

To prepare the hydroxide form of the above organic salt: 10 g of organic salt is dissolved in 75 g of water. Next, 40 g of an anion exchange resin (Dower SBR) are added and the resulting mixture is kept under stirring for 24 hours. Finally, the solution is filtered and the N,N-diethyl-2,6-dimethylpiperidine hydroxide (with a percentage of 90% exchange) is obtained.

Example 3

Synthesis of the SAPO-18 material using DMDMP as OSDA

First, 1324.3 mg of orthophosphoric acid (85% by weight, Aldrich) is mixed with 6287.0 mg of an aqueous solution at 19% by weight of DMDMP hydroxide and kept under stirring for 10 minutes. Next, 1043.8 mg of alumina (75% by weight, Condea) and 304.2 mg of a colloidal silica suspension (Ludox AS40 40% by weight, Aldrich) are introduced. The resulting mixture is kept under stirring for the required time to evaporate the excess of water to achieve the desired gel concentration. The final composition of the gel is:

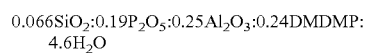

The gel is transferred to a Teflon-lined autoclave, and heated at 190° C. for 2 days under dynamic conditions. After the hydrothermal crystallization process, the sample is filtered and washed with abundant distilled water and finally dried at 100° C.

The sample is characterised by X-ray diffraction (XRD), observing the formation of the characteristic XRD pattern of SAPO-18 (see FIG. 1).

Figure 2:
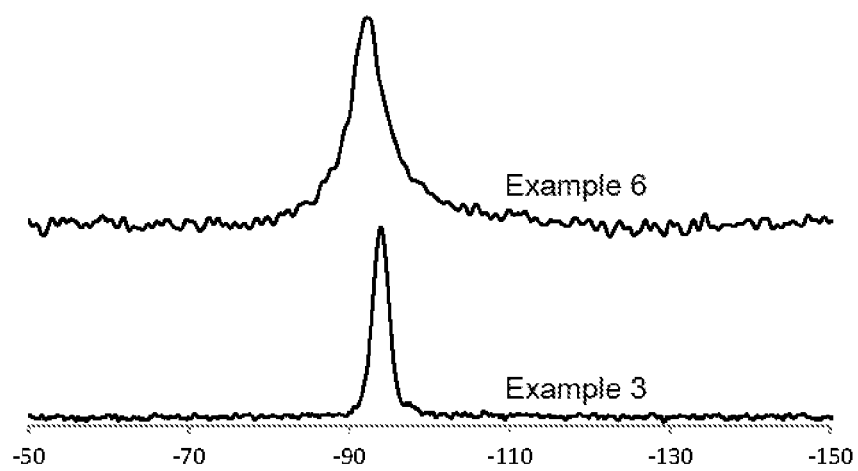
FIG. 2: Solid $^{29}$Si Nuclear magnetic resonance (NMR) spectra of synthesized samples according to Examples 3 and 6.

As evidenced by the solid $^{29}$Si nuclear magnetic resonance (NMR), the synthesized SAPO-18 shows only the presence of isolated silicon species in its structure (see the band centred at −90 ppm in the sample Example 3 in FIG. 2).

The sample is calcinated at 550° C. in air to remove the organic matter fractions occluded in the interior of the microporous material during the crystallization process.

Example 4

Synthesis of SAPO-18 Material using DMDMP as OSDA

First, 1365.3 mg of orthophosphoric acid (85 wt %, Aldrich) is mixed with 6282.0 mg of an aqueous solution at 19% by weight of DMDMP hydroxide and kept under stirring for 10 minutes. Next, 1016.3 mg of alumina (75% by weight, Condea) and 195.3 mg of a colloidal silica suspension (Ludox AS40 40% by weight, Aldrich) are introduced. The resulting mixture is kept under stirring for the required time to evaporate the excess of water to achieve the desired gel concentration. The final composition of the gel is:

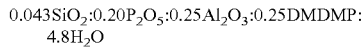

0.043$SiO_2$:0.20$P_2O_5$:0.25$Al_2O_3$:0.25DMDMP: 4.8$H_2O$

The gel is transferred to a Teflon-lined autoclave and heated at 190° C. for 2 days under dynamic conditions. After the hydrothermal crystallization process, the sample is filtered and washed with abundant distilled water and finally dried at 100° C.

The sample is characterised by X-ray diffraction to determine the structure obtained after the crystallization process, observing the characteristic diffraction pattern of SAPO-18.

The sample is calcinated at 550° C. in air to remove organic matter fractions occluded in the interior of the microporous material during the crystallization process.

Example 5

Synthesis of SAPO-18 Material using DEDMP as OSDA

First 107.5 mg of orthophosphoric acid (85 wt %, Aldrich) is mixed with 712.2 mg of an aqueous solution at 15% by weight of DEDMP hydroxide and kept under stirring for 10 minutes. Next, 83.5 mg of alumina (75% by weight, Condea) and 17.9 mg of a colloidal silica suspension (Ludox AS40 40% by weight, Aldrich) are introduced. The resulting mixture is kept under stirring for the required time to evaporate the excess of water until the gel reaches the desired concentration of the gel. The final composition of the gel is:

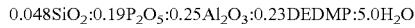

0.048$SiO_2$:0.19$P_2O_5$:0.25$Al_2O_3$:0.23DEDMP:5.0$H_2O$

The gel is transferred to a Teflon-lined autoclave, and heated at 190° C. for two days under dynamic conditions. After the hydrothermal crystallization process, the sample is filtered and washed with abundant distilled water and finally dried at 100° C.

The sample is characterised by X-ray diffraction to determine the structure obtained after the crystallization process, observing the characteristic diffraction pattern of SAPO-18.

The sample is calcinated at 550° C. in air to remove organic matter fractions occluded in the interior of the microporous material during the crystallization process.

Example 6

Direct Synthesis of the Cu-SAPO-18 Material using Cu Triethylenetetramine (Cu-TETA) as a Precursor of Cu and DMDMP as OSDA The first step is the preparation of the Cu-TETA copper complex. To this end, 405.9 mg of a 20% aqueous solution by weight of copper sulphate (II) (98% by weight, Alfa) is mixed with 74.5 mg of triethylenetetramine (TETA, 99% by weight, Aldrich) and kept under stirring for 2 hours. Next, 2700 mg of distilled water and 1035.8 mg of orthophosphoric acid (85% by weight, Aldrich) are added and the resulting solution is kept under stirring for 5 minutes. Finally, 8840 mg of an aqueous solution at 17.1% by weight of DMDMP hydroxide is added, and kept under stirring another 5 minutes. Finally, 734.7 mg of alumina (75% by weight, Condea) and 241.5 mg of a colloidal silica suspension (Ludox AS40 40% by weight, Aldrich) are introduced. The resulting mixture is stirred for 30 minutes or the required time to evaporate the excess of water to achieve the desired gel concentration. The final composition of the gel is:

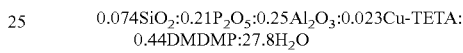

0.074$SiO_2$:0.21$P_2O_5$:0.25$Al_2O_3$:0.023Cu-TETA: 0.44DMDMP:27.8$H_2O$

The gel is transferred to a Teflon-lined autoclave, and heated at 175° C. for 6 days under dynamic conditions. After the hydrothermal crystallization process, the sample is filtered and washed with abundant distilled water and finally dried at 100° C.

The sample was characterised by X-ray diffraction to determine the structure obtained after the crystallization process (see the XRD pattern in FIG. 1).

Figure 3:
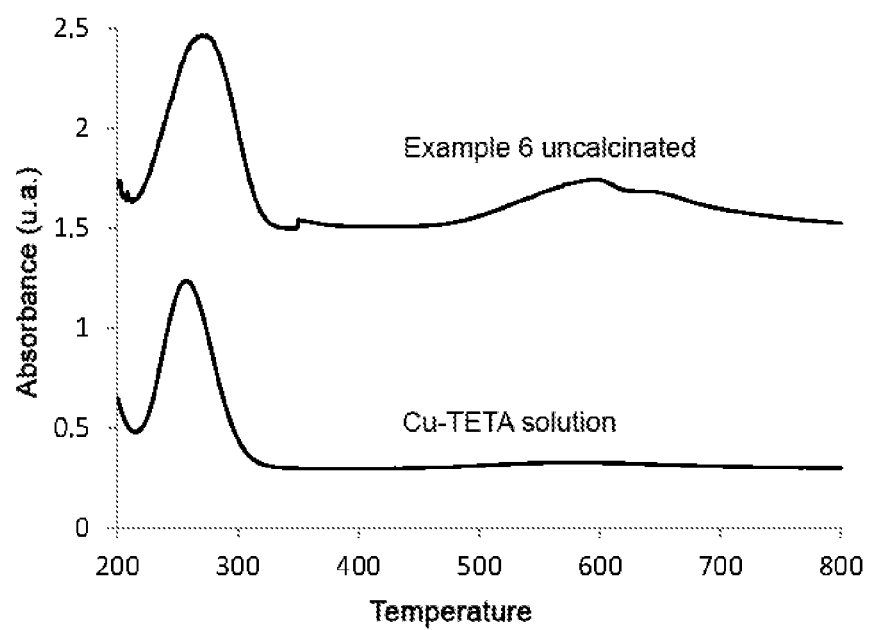
FIG. 3: UV-Vis spectra of the sample synthesized in Example 6 of the present invention in its uncalcinated form and of the Cu-TETA complex in an aqueous solution.

The as-prepared sample is characterised by ultraviolet-visible (UV-Vis) spectroscopy to verify that the copper atoms are in extra-network positions. The UV-Vis spectrum of the sample in its uncalcinated form shows a single band centred at ~260 nm, which shows the presence of the intact organometallic complex within the solid in extra-framework positions (see FIG. 3).

As shown by the solid $^{29}$Si nuclear magnetic resonance (NMR) spectrum, the synthesized SAPO-18 only shows the presence of isolated silicon species in its structure (see the band centred at −90 ppm in the sample Example 6 in FIG. 2).

The sample is calcinated at 550° C. in air to remove the organic matter fractions occluded in the interior of the microporous material during the crystallization process.

Example 7

Direct Synthesis of the Cu-SAPO-18 Material using Cu Triethylenetetramine (Cu-TETA) as a Precursor of Cu and DMDMP as OSDA The first step is the preparation of the Cu-TETA copper complex. To this end, 799.2 mg of a 20% aqueous solution by weight of copper sulphate (II) (98 wt %, Alfa) is mixed with 145.5 mg of triethylenetetramine (TETA, 99% by weight, Aldrich) and kept under stirring for 2 hours. Next, 2800 mg of distilled water and 1043.2 mg of orthophosphoric acid (85% by weight, Aldrich) are added and the resulting solution is kept under stirring for 5 minutes. Subsequently, 8405 mg of an aqueous solution at 17.1% by weight of DMDMP hydroxide is added and kept under stirring another 5 minutes. Finally, 734.5 mg of alumina (75% by weight, Condea) and 254.2 mg of a colloidal silica suspension (Ludox AS40 40% by weight, Aldrich) are introduced. The resulting mixture is stirred for 30 minutes or the required time to evaporate the excess of water to achieve the desired gel concentration. The final composition of the gel is:

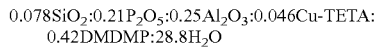
$$0.078SiO_2:0.21P_2O_5:0.25Al_2O_3:0.046Cu\text{-TETA}:$$
$$0.42DMDMP:28.8H_2O$$

The gel is transferred to a Teflon-lined autoclave and heated at 175° C. for 6 days under dynamic conditions. After the hydrothermal crystallization process, the sample is filtered and washed with abundant distilled water and finally dried at 100° C.

The sample is characterised by X-ray diffraction to determine the structure obtained after the crystallization process, observing the characteristic diffraction pattern of SAPO-18.

The sample is calcinated at 550° C. in air to remove the organic matter fractions occluded in the interior of the microporous material during the crystallization process.

Example 8

Direct Synthesis of the Cu-SAPO-18 Material using Cu-Triethylenetetramine (Cu-TETA) as a Precursor of Cu and DMDMP as OSDA The first step is the preparation of the Cu-TETA copper complex. To do this, 1591.4 mg of a 20% aqueous solution by weight of copper sulphate (II) (98% by weight, Alfa) is mixed with 296.4 mg of triethylenetetramine (TETA, 99% by weight, Aldrich) and kept stirring for 2 hours. Next, 1056.0 mg of orthophosphoric acid (85% by weight, Aldrich) is added and the resulting solution is kept under stirring for 5 minutes. Subsequently, 10031 mg of an aqueous solution at 12.2% by weight of DMDMP hydroxide is added and is kept under stirring for another 5 minutes. Finally, 735.0 mg of alumina (75% by weight, Condea) and 242.1 mg of a colloidal silica suspension (Ludox AS40 40% by weight, Aldrich) are introduced. The resulting mixture is stirred for 30 minutes or the required time to evaporate the excess of water to achieve the desired gel concentration. The final composition of the gel is:

$$0.074SiO_2:0.21P_2O_5:0.25Al_2O_3:0.093Cu\text{-TETA}:$$
$$0.36DMDMP:29.3H_2O$$

The gel is transferred to a Teflon-lined autoclave and heated at 175° C. for 6 days under dynamic conditions. After the hydrothermal crystallization process, the sample is filtered and washed with abundant distilled water and finally dried at 100° C.

The sample was characterised by X-ray diffraction to determine the structure obtained after the crystallization process, observing the characteristic diffraction pattern of SAPO-18.

The sample is calcinated at 550° C. in air to remove the organic matter fractions occluded in the interior of the microporous material during the crystallization process.

Example 9

Direct Synthesis of Cu-SAPO-18 Material using Cu-Triethylenetetramine (Cu-TETA) as Precursor of Cu and DMDMP as OSDA The first step is the preparation of the Cu-TETA copper complex. To this end, 400.8 mg of an aqueous solution 20% by weight of copper sulphate (II) (98% by weight, Alfa) with 72.9 mg of triethylenetetramine (TETA, 99% by weight, Aldrich) are added and kept under stirring for 2 hours. Next, 1076.8 mg of orthophosphoric acid (85% by weight, Aldrich) is added and the resulting solution is kept under stirring for 5 minutes. Subsequently, 8692 mg of an aqueous solution at 17.4% by weight of DMDMP hydroxide is added and kept under stirring for another 5 minutes. Finally, 734.5 mg (75% by weight, Condea) and 251.6 mg of a colloidal silica suspension (Ludox AS40 40% by weight, Aldrich) are introduced. The resulting mixture is kept under stirring for 30 minutes or the required timeto evaporate the excess of water to achieve the desired gel concentration. The final composition of the gel is:

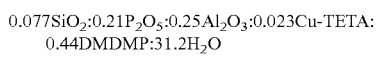
$$0.077SiO_2:0.21P_2O_5:0.25Al_2O_3:0.023Cu\text{-TETA}:$$
$$0.44DMDMP:31.2H_2O$$

The gel is transferred to a Teflon-lined autoclave, and heated at 190° C. for 3 days under dynamic conditions. After the hydrothermal crystallization process, the sample is filtered and washed with abundant distilled water and finally dried at 100° C.

The sample was characterised by X-ray diffraction to determine the structure obtained after the process, observing the characteristic diffraction pattern of SAPO-18.

The sample is calcinated at 550° C. in air to remove the organic matter fractions occluded in the interior of the microporous material during the crystallization process.

Example 10

Direct Synthesis of the Cu-SAPO-18 Material using Cu-Triethylenetetramine (Cu-TETA) as a Precursor of Cu and DMDMP as OSDA The first step is the preparation of the Cu-TETA copper complex. To this end, 799.2 mg of an aqueous solution 20% by weight of copper sulphate (II) (98% by weight, Alfa) is mixed with 145.4 mg of triethylenetetramine (TETA, 99% by weight, Aldrich) and kept under stirring for 2 hours. Next, 1061.6 mg of orthophosphoric acid (85% by weight, Aldrich) is added and the resulting solution is kept under stirring for 5 minutes. Subsequently, 8244 mg of an aqueous solution at 17.4% by weight of DMDMP hydroxide is added and kept under stirring another 5 minutes. Finally, 735.4 mg of alumina (75% by weight, Condea) and 248.1 mg of a colloidal silica suspension (Ludox AS40 40% by weight, Aldrich) are introduced. The resulting mixture is stirred for 30 minutes or the required time to evaporate the excess of water to achieve the desired gel concentration. The final composition of the gel is:

$$0.076SiO_2:0.21P_2O_5:0.25Al_2O_3:0.046Cu\text{-TETA}:$$
$$0.42DMDMP:32.5H_2O$$

The gel is transferred to a Teflon-lined autoclave, and heated at 190° C. for 3 days under dynamic conditions. After the hydrothermal crystallization process, the sample is filtered and washed with abundant distilled water and finally dried at 100° C.

The sample was characterized by X-ray diffraction to determine the structure obtained after the crystallization process, observing the characteristic diffraction pattern of SAPO-18.

The sample is calcinated at 550° C. in air to remove the organic matter fractions occluded in the interior of the microporous material during the crystallization process.

Example 11

Chemical Analysis of Various Cu-SAPO-18 Materials obtained herein

Molar ratios of Si and Cu obtained by ICP of the materials synthesized in examples 6, 7, 8, 9 and 10 (see Table 1).

TABLE 1

Molar ratios of solids synthesized according to Examples 7, 8 and 9 of the present invention.

| Example | Si/(Al + P) | Cu/(Al + P) |
|---|---|---|
| 5 | 0.097 | 0.028 |
| 7 | 0.101 | 0.058 |
| 8 | 0.104 | 0.063 |
| 9 | 0.089 | 0.029 |
| 10 | 0.090 | 0.064 |

Example 12

Thermal Treatments in the Presence of Steam

The hydrothermal stability of some of the samples synthesized in the examples of the present invention is studied by treating them with steam (2.2 ml/min) at 750° C. for 13 hours.

Example 13

Catalytic Test for the SCR of NOx Reaction using Different Cu-SAPO-18 Materials Synthesized According to the Present Invention The activity of these samples for the selective catalytic reduction of NOx is studied using a tubular fixed-bed quartz reactor 1.2 cm in diameter and 20 cm long. In a typical experiment, the catalyst is compacted into particles in the size range of 0.25 to 0.42 mm, which are introduced into the reactor, and the temperature is increased to 550° C. (see the reaction conditions in Table 2); subsequently, the temperature is maintained for 1 hour under nitrogen flow. Once the desired temperature has been reached, the reactive mixture is fed. The SCR of NOx is studied using $NH_3$ as a reducing agent. The NOx present in the gases that flow out of the reactor is continuously analysed using a chemiluminescent detector (Thermo 62C).

TABLE 2

Reaction conditions of SCR of NOx.

| | |
|---|---|
| Total gas flow (ml/min) | 300 |
| Catalyst load (mg) | 40 |
| Concentration of NO (ppm) | 500 |
| Concentration of $NH_3$ (ppm) | 530 |
| Concentration of $O_2$ (%) | 7 |
| Concentration of $H_2O$ | 5 |
| Temperature interval tested (° C.) | 170-550 |

The catalytic results of some of the catalysts synthesized in any of the examples of the present invention are summarised in Table 3. In Table 3, the catalytic results of the materials synthesized in examples 7, 9 and 10, after being treated with steam, are also described They are treated with steam at 750° C. for 13 hours (Example 7-750° C., Example 9-750° C. and 10-750° C., respectively).

TABLE 3

Conversion (%) of NOx at different temperatures (200, 250, 300, 350, 400, 450, 500° C.) using the various Cu-SAPO-18 materials synthesized following the synthesis methodology described herein.
Conversion (%) of NOx at different temperatures

| | 210° C. | 250° C. | 300° C. | 350° C. | 400° C. | 450° C. | 500° C. | 550° C. |
|---|---|---|---|---|---|---|---|---|
| Example 6 | 63.1 | 82.0 | 81.2 | 82.6 | 87.4 | 90.6 | 83.5 | 52.9 |
| Example 7 | 79.0 | 93.5 | 94.1 | 94.3 | 94.3 | 91.9 | 78.2 | 54.9 |
| Example 8 | 75.9 | 85.5 | 85.8 | 87.2 | 89.4 | 89.3 | 75.2 | 47.2 |
| Example 7-750° C. | 84.6 | 92.9 | 91.5 | 91.7 | 90 | 88.3 | 74.6 | 61.1 |
| Example 9-750° C. | 84.6 | 93.3 | 90.9 | 92.4 | 92.2 | 93.9 | 89.1 | 82.2 |
| Example 10-750° C. | 93.2 | 99 | 98.6 | 99.4 | 98.4 | 97.1 | 88.7 | 82.6 |

The invention claimed is:

1. A procedure for the synthesis of SAPO-18 comprising the following steps:
   i) preparing a mixture containing at least water, at least one source of silicon, at least one source of aluminum, at least one source of phosphorus, one or more organic structure-directing agents (OSDA), wherein at least one OSDA is a cyclic quaternary ammonium, and where the mixture has the following molar composition:

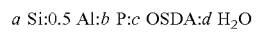

$a$ Si:0.5 Al:$b$ P:$c$ OSDA:$d$ $H_2O$ where a is between the interval 0.01 to 0.3;
   where b is between the interval 0.2 to 0.49;
   where c is between the interval 0.001 to 2;
   where d is between the interval 1 to 200;
   ii) hydrothermally treating the mixture at a temperature between 80-200° C. until a crystalline material is formed, and
   iii) recovering the crystalline material.

2. The procedure of claim 1, wherein the mixture has the following molar composition:

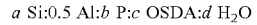

$a$ Si:0.5 Al:$b$ P:$c$ OSDA:$d$ $H_2O$ where a is between the interval 0.03 to 0.3;
   where b is between the interval 0.2 to 0.47;
   where c is between the interval 0.1 to 1;
   where d is between the interval 2 to 200.

3. The procedure claim 1, wherein the cyclic quaternary ammonium is selected from the group consisting of N,N-dimethyl-3,5-dimethylpiperidine (DMDMP), N,N-diethyl- 2,6-dimethylpiperidine (DEDMP), N,N-dimethyl-2,6-dimethylpiperidine, N-ethyl-N-methyl-2,6-dimethylpiperidine and combinations thereof.

4. The procedure of claim 1, wherein step (ii) is carried out in an autoclave under both static and dynamic conditions.

5. The procedure of claim 1, wherein the temperature of step (ii) is within the temperature range of 100 and 200° C.

6. The procedure of claim 1, wherein in step (ii) the mixture is hydrothermally treated between 1 hour and 50 days.

7. The procedure of claim 1, wherein crystals of the SAPO-18 material are added to the mixture as seed after step (i) but before step (ii).

8. The procedure of claim 7, wherein the amount of SAPO-18 crystals is up to 25% by weight of the total components introduced in the synthesis.

9. The procedure of claim 1, wherein in step (iii) the crystalline material is separated from a mother liquor by decantation, filtration, ultrafiltration, centrifugation, a solid-liquid separation technique and combinations thereof.

10. The procedure of claim 1, further comprising removing an organic matter occluded in the interior of the material.

11. The procedure of claim 10, wherein the removal of the organic matter is carried out by extraction, thermal treatment or combinations thereof and at a temperature above 25° C. between 2 minutes and 25 hours.

12. The procedure of claim 1, wherein the crystalline material is pelletized.

13. The procedure of claim 1, wherein the mixture further comprises, at least one source of metal (X) where the mixture has the following molar composition:

$a$ Si:0.5 Al:$b$ P:$e$ X:$c$ OSDA:$d$ H$_2$O where a is between the interval 0.01 to 0.3;

where b is between the interval 0.2 to 0.49;
where c is between the interval 0.001 to 2;
where d is between the interval 1 to 200;
where e is between the interval 0.00 to 0.6.

14. The procedure of claim 13, wherein the procedure is a direct synthesis procedure and the product Me-SAPO-18 is obtained, wherein Me is metal X.

15. The procedure of claim 14, wherein said metal is selected from the group consisting of Cu, Ni, Fe, Pt, Pd, Mn, Ca, Mg, Zn, Cd, Co, Ti, Sn and combinations thereof.

16. The procedure of claim 15, wherein said metal is Cu.

17. A product obtained by the procedure of claim 13, wherein the product has the following molar composition:

$X_{0.0-0.6}Si_{0.01-0.3}Al_{0.40-0.55}P_{0.20-0.49}O_2$.

18. The product of claim 17, wherein the product has the following molar composition:

$X_{0.005-0.6}Si_{0.01-0.3}Al_{0.40-0.55}P_{0.20-0.49}O_2$.

19. The product of claim 18, wherein X is a metal selected from the group consisting of Cu, Ni, Fe, Pt, Pd, Mn, Ca, Mg, Zn, Cd, Co, Ti, Sn and combinations thereof.

20. The product of claim 19, wherein said metal is Cu.

21. The product of claim 19, wherein the metal is in extra-network positions.

22. A catalyst for the removal or separation of organic compounds from the reactive current comprising the product of claim 17.

23. A catalyst for converting feed formed by organic compounds into high value-added products comprising the product of claim 17.

24. A catalyst for the selective reduction of nitrogen oxides in a gas stream, wherein the catalyst comprises the product of claim 17.

* * * * *